United States Patent [19]
Tomura

[11] Patent Number: 5,184,622
[45] Date of Patent: Feb. 9, 1993

[54] ULTRASONIC DIAGNOSING APPARATUS
[75] Inventor: Hidesuke Tomura, Tochigi, Japan
[73] Assignee: Kabushiki Kaisha Toshiba, Kawasaki, Japan
[21] Appl. No.: 645,397
[22] Filed: Jan. 24, 1991
[30] Foreign Application Priority Data
  Jan. 24, 1990 [JP] Japan ................... 2-12475
[51] Int. Cl.$^5$ ............................... A61B 8/00
[52] U.S. Cl. .................. 128/660.07; 128/660.01
[58] Field of Search .............. 128/660.01, 660.07, 128/661.07, 661.01, 660.05

[56] References Cited
U.S. PATENT DOCUMENTS

| | | | |
|---|---|---|---|
| 4,062,237 | 12/1977 | Fox | 128/660.05 |
| 4,790,321 | 12/1988 | Miwa et al. | 128/660.07 |
| 4,865,040 | 9/1989 | Ogasawara | 128/660.01 |
| 4,880,010 | 11/1989 | Szilard | 128/661.01 |
| 5,060,515 | 10/1991 | Kanda et al. | 128/660.01 |

Primary Examiner—Francis Jaworski
Assistant Examiner—George Manuel
Attorney, Agent, or Firm—Oblon, Spivak, McClelland, Maier & Neustadt

[57] ABSTRACT

An ultrasonic diagnosing apparatus including an ultrasonic transducer for transmitting an ultrasonic beam to a subject and converting echoes from the subject to echo signals, a transmitter/receiver circuit for driving the ultrasonic transducer, an image processor signal processing the echo signals output from the ultrasonic transducer to output an ultrasonic image signal, a memory for storing body-mark pattern data indicating a first body-mark, a body-mark processor for processing the body-mark pattern data so that a part of the first body-mark pattern is designated as a second body-mark pattern, and a display for displaying the ultrasonic image and the body-mark pattern from the body-mark processor.

14 Claims, 2 Drawing Sheets

5,184,622

ULTRASONIC DIAGNOSING APPARATUS

BACKGROUND OF THE INVENTION

Field of the Invention

The present invention relates to an ultrasonic diagnosing apparatus for displaying an ultrasonic image and a body-mark pattern which illustrates an examined position corresponding to the ultrasonic image, i.e. a position of the transducer on a patient.

Description of the Background

An ultrasonic diagnosing apparatus which can display a body-mark pattern is well known. In such an apparatus, a plurality of body-mark patterns (for example, a body-mark pattern of the head, breast, or abdomen, etc.) are stored in a memory of the apparatus. By selecting one among the body-mark patterns stored in the memory, an operator is able to choose to be displayed a body-mark pattern which shows that part of the body corresponding to the ultrasonic image displayed. It is thereby possible for the operator to recognize which part of the body was examined by the ultrasonic image, when the operator records the ultrasonic image accompanying the body-mark pattern.

An operator can produce his own new original body-mark patterns in addition to those stored in the memory in some conventional apparatuses. Such original body-mark patterns are made by changing data in the memory. Otherwise, the operator can draw a completely new body-mark pattern on the display by operating a keyboard or a trackball of the apparatus.

However, it is troublesome for an operator to make his own original body-mark patterns by himself, in particular, during clinical examination, and the number of the body-mark patterns stored in the memory is limited by the memory size. In other words, it is necessary for the operator to make the original body-mark patterns required by the operator when that body-mark pattern is not stored in a body-mark memory, or it is necessary for the ultrasonic diagnosing apparatus to have a large capacity memory to store many body-mark patterns.

SUMMARY OF THE INVENTION

It is an object of the present invention to provide an ultrasonic diagnosing apparatus which allows an operator easily to make his original body-mark patterns when the body-mark pattern required by the operator is not stored in the body-mark memory.

In order to achieve the above object, according to the present invention, there is provided an ultrasonic diagnosing apparatus including an ultrasonic transducer for transmitting an ultrasonic beam to a subject and converting echoes from the subject to echo signals; a transmitter/receiver coupled to the ultrasonic transducer for driving the ultrasonic transducer; an image processor for signal processing the echo signals output from the ultrasonic transducer means and outputting an ultrasonic image signal; a memory for storing body-mark pattern data indicating a first body-mark pattern; a body-mark processor for processing the body-mark pattern data so that a part of the first body-mark pattern is designated as a second body-mark pattern; and a display for displaying the ultrasonic image signal from the image processing means and the second body-mark pattern from the body-mark processing means.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
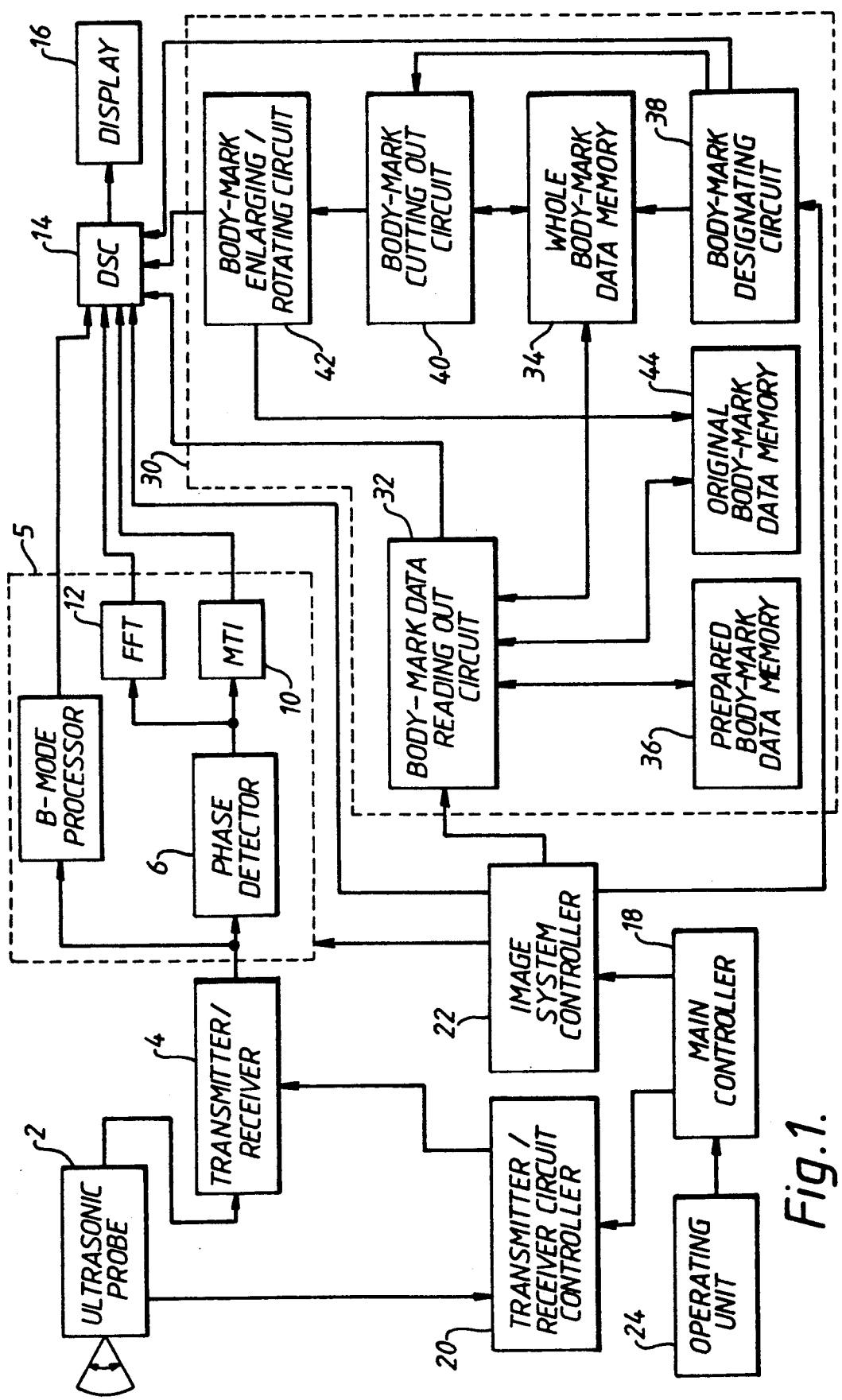
FIG. 1 is a block diagram showing an arrangement of an ultrasonic diagnosing apparatus capable of producing original body-mark patterns on a display according to an embodiment of the present invention.

Referring now to FIG. 1, an ultrasonic diagnosing apparatus according to an embodiment of the present invention includes an ultrasonic probe 2 including an ultrasonic transducer which transmits ultrasonic pulses and receives ultrasonic pulses from a subject under examination, and which is connected to a transmitter/receiver circuit 4. The transmitter/receiver circuit 4 applies driving pulses to the ultrasonic probe 2 so as to transmit ultrasonic waves to the subject and receive echo signals from the ultrasonic probe 2 for subsequent processing.

A phase detector 6, which is connected to the transmitter/receiver circuit 4, phase-detects a received signal from the transmitter/receiver circuit 4 to output a Doppler shift signal. An MTI (moving target indicator) 10, which is also called a CFM (color flow mapping) unit, filters an output signal of the phase detector 6 to extract a Doppler signal only and amount of blood flow. An FFT (fast Fourier transformer) 12 analyzes frequency components of a blood flow signal from the phase detector 6 to obtain a frequency spectrum. A B-mode processing circuit 8 detects a B-mode signal from the received signal from the transmitter/receiver circuit 4. The detected B-mode signal is output to a DSC (digital scan converter) 14. The DSC 14 receives and stores output signals of the B-mode processing circuit 8, the MTI 10 and the FFT 12 for conversion to a TV scan signal which is, in turn, output to a display 16.

A main controller 18 supplies control signals to a transmitter/receiver circuit controller 20 and an image system controller 22 in accordance with scan instructions from an operator. An operating unit 24 may include a keyboard or a trackball, and supplies operating signals to the main controller 18.

In response to control signals from the main controller 18, the transmitter/receiver circuit controller 20 supplies control signals and probe driving frequency corresponding to the probe information of the probe 2 to the transmitter/receiver circuit 4. The transmitter/receiver circuit 4 drives the probe 2 with the probe driving frequency corresponding to the probe information.

The image system controller 22 supplies control signals to the image processor circuit 5, a body-mark processor circuit 30, and also supplies data write/read control signals to the DSC 14.

In response to the control signals from the image system controller 22, the body-mark processor circuit 30 outputs a body-mark data signal to the DSC 14.

The body-mark processor circuit 30 includes a body-mark data reading out circuit 32 which reads out the body-mark pattern data of a whole body from a whole body-mark data memory 34, the body-mark pattern data prepared by a manufacturer from a prepared body-mark data memory 36, and the body-mark pattern data made by an operator from an original body-mark data memory 44 to DSC 14 in correspondence with the control signals from the image system controller 22.

Figure 2:
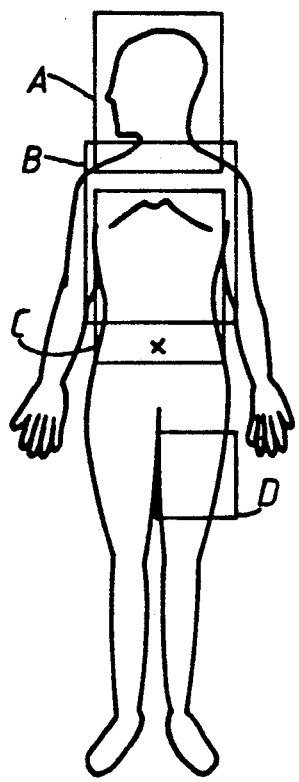
FIG. 2 is a illustrative representation showing a body-mark pattern of a whole body which is to be processed for making an original body-mark pattern according to the present invention.

FIG. 2 shows an example of a body-mark pattern of a whole body. The body-mark pattern of the whole body may be a right, a left or a front view of a man. In addition, it may be plural views of a man, or may be a intracavity view of a man, or may be a view of a nonhuman.

A body-mark designating circuit 38 is for designating a part of the body-mark pattern of the whole body on the display 16, and this designated data is output to a body-mark cutting out circuit 40. The body-mark cutting out circuit 40 is provided for cutting out a part of the body-mark pattern data for the whole body corresponding to the designated data from the body-mark designating circuit 38, and this cutout data is output to a body-mark enlarging/rotating circuit 42. The body-mark enlarging/rotating circuit 42 is provided for enlarging size and for rotating the cutout body-mark pattern data to a desired or discretionary angle on the display 16. The body-mark enlarging/rotating circuit 42 outputs the data to DSC 14 and to an original body-mark data memory 44.

The operation of the above-described embodiment will now be described. Ways to designate a part of the body-mark pattern of the whole body are described in relation to FIGS. 3A and 3B.

First, a body-mark of a whole body is displayed on the display 16. More specifically, the whole body-mark data memory 34 is accessed by the body-mark data reading out circuit 32 and data of a body-mark of a whole body is read out from the whole body-mark data memory 34. The read out data is converted to an image signal and an image of a whole body is displayed on the display 16.

Figure 3A:
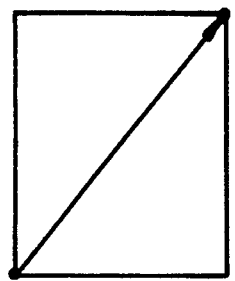
FIGS. 3A and 3B are illustrative representations explaining ways to determine an area representing a part of the whole body-mark pattern shown in FIG. 2 for making an original body-mark according to the present invention.
Figure 4A:
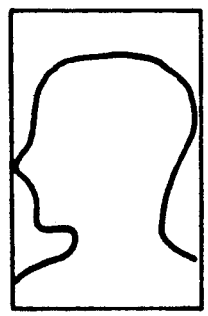
FIGS. 4A to 4D are illustrative representations for explaining examples of original body-mark patterns according to the embodiment.

Second, using the way shown in FIG. 3A in the case of making an original body-mark pattern of the head (shown in FIG. 4A), an operator designates a location of a dot cursor at a right shoulder of the body-mark pattern of the whole body on the display 16 by the operating unit 24. Next, the operator moves a cursor to display a square line marker in which the above designated point and the present cursor are located diagonally of the square on the display 16. When the operator moves the cursor to the top-left of the head, the square area which contains the head is designated as an original body-mark pattern of the head. These designated data are output to the body-mark cutting out circuit 40 from the body-mark designating circuit 38, and the body-mark cutting out circuit 40 cuts out the body mark data, which is a part of the body-mark pattern of the whole body, corresponding to the designated data from body-mark designating circuit 38. The cutout data is output to the body-mark enlarging/rotating circuit 42 and the body-mark pattern made from the cutout data is enlarged to a fixed size and rotated to a desired angle on the display 16. In the manner described above, an original body-mark pattern of the head can be displayed on the display 16.

Figure 3B:
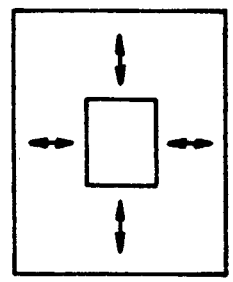

Otherwise, as is evident from FIG. 3B, an operator moves a square cursor, which size can be changed, to a center of the head part of the body-mark pattern of the whole body and designates its location. Next, the operator changes the size of the square cursor on the display 16 by the operating unit 24 and designates the square area for creating an original body-mark pattern of the head (shown in FIG. 4A).

Figure 4B:
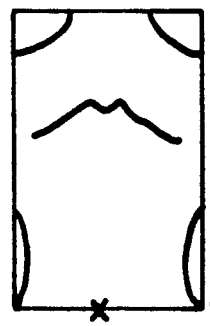
Figure 4C:
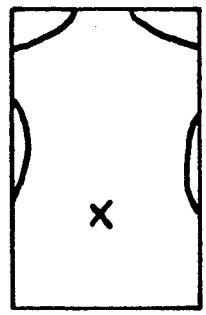
Figure 4D:
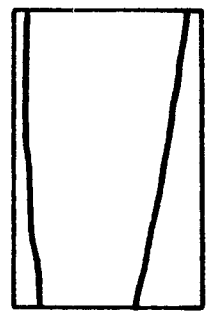

FIGS. 4B to 4D show original body-mark patterns of the breast, the abdomen, and the femoral region according to the embodiment of the present invention and these original body-mark patterns are made by means of the above techniques.

According to the present embodiment, as described above, by selecting the area which is a part of the body-mark pattern data of the whole body from the whole body-mark data memory 34, an operator easily can make an original body-mark pattern of any part of a body corresponding to the ultrasonic image, display it in addition to the ultrasonic image on the same display 16, and store it in the original body-mark data memory 44. Thus, any operator is easily able to recognize what part of the body is examined by the ultrasonic image on the display 16 without the requirement of a large memory for so many prepared body-mark patterns.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An ultrasonic diagnosing apparatus comprising:
   ultrasonic transducer means for transmitting an ultrasonic beam to a subject and converting echoes from the subject to echo signals;
   transmitter/receiver means coupled to said ultrasonic transducer means for driving said ultrasonic transducer means;
   image processing means for signal processing said echo signals output from said ultrasonic transducer means to output an ultrasonic image signal representative of a portion of said subject;
   memory means for storing predetermined body-mark pattern data indicating a first body-mark pattern;
   body-mark processing means for processing said body-mark pattern data so that a part of said body-mark pattern is designated as a second body-mark pattern corresponding to said portion of said subject;
   display means for displaying said ultrasonic image signal from said image processing means and said second body-mark pattern corresponding to said portion of said subject from said body-mark processing means on a monitor.

2. An apparatus according to claim 1, wherein said body-mark processing means comprises:
   a body-mark designating means for designating a part of said first body-mark pattern for making said second body-mark pattern.

3. An apparatus according to claim 2, wherein:
said display means comprises means for displaying said first body mark pattern; and
said body-mark designating means comprises means for designating an area on a displayed first body-mark pattern using two operator controlled diagonals.

4. An apparatus according to claim 3, wherein said memory means includes means for storing body-mark pattern data of a whole body.

5. An apparatus according to claim 2, wherein:
said displaying means comprises means for displaying said first body mark pattern; and
said body-mark designating means comprises cursor means for designating an area on a displayed first body-mark pattern, and means for changing a size of the area designated by said cursor means.

6. An apparatus according to claim 5, wherein said memory means includes means for storing body-mark pattern data of a whole body.

7. An apparatus according to claim 2, wherein said body-mark processing means comprises:
a body-mark cutting out means for cutting out a part of said body-mark pattern data corresponding to said part of said first body-mark pattern designated by said body-mark designating means.

8. An apparatus according to claim 7, wherein said body-mark processing means comprises:
a body-mark enlarging/rotating means for enlarging a body-mark pattern represented by said part of said body-mark pattern data cutout by said body-mark cutting out means to be a fixed size and for rotating said enlarged body-mark pattern to a desired angle displayed on the display means by means of control signals from an operating means.

9. An apparatus according to claim 8, wherein said memory means includes means for storing body-mark pattern data of a whole body.

10. An apparatus according to claim 9, wherein said memory means includes means for storing a plurality of said predetermined body-mark data, and means for storing a plurality of body-mark data produced by said body-mark enlarging/rotating means.

11. An apparatus according to claim 8, wherein said memory means includes means for storing a plurality of said predetermined body-mark data and means for storing a plurality of body-mark pattern data produced by said body-mark enlarging/rotating means.

12. An apparatus according to claim 7, wherein said memory means includes means for storing body-mark pattern data of a whole body.

13. An apparatus according to claim 2, wherein said memory means includes means for storing body-mark pattern data of a whole body.

14. An apparatus according to claim 1, wherein said memory means includes means for storing body-mark pattern data of a whole body.

* * * * *